United States Patent [19]

Mego

[11] 4,271,326
[45] Jun. 2, 1981

[54] METHOD OF PROCESSING ORGANIC WASTE INTO USEFUL PRODUCTS

[76] Inventor: Ronald M. Mego, P.O. Box 325, Leechburg, Pa. 15656

[21] Appl. No.: 77,908

[22] Filed: Sep. 24, 1979

[51] Int. Cl.$^3$ .............................................. C07C 4/00
[52] U.S. Cl. ..................................... 585/240; 203/33; 201/2.5; 252/1
[58] Field of Search ............... 210/71; 201/2.5, 25, 201/45; 208/8, 9; 44/1 D, 1 E; 48/197 R, 197 A, 209, DIG. 7; 260/683 PD; 162/30 R, 30 K; 71/14; 202/105, 107, 112, 210, 217, 226; 203/33; 585/240; 252/1

[56] References Cited

U.S. PATENT DOCUMENTS

| | | | |
|---|---|---|---|
| 3,864,097 | 2/1975 | Urban | 201/2.5 |
| 4,073,660 | 2/1978 | Portnoy | 201/2.5 |

OTHER PUBLICATIONS

C & E News; "From Agricultural Wastes to Feed or Fuel"; May 29 1972; Crentz; pp. 14 and 15.

*Primary Examiner*—Frank Sever

[57] ABSTRACT

A method of treating organic waste involves slurrying the organic waste in water with a member selected from the group consisting of potassium carbonate, ammonium nitrate and ammonium nitrite. The slurry is heated to a temperature of 100° C. to 430° C. After heating, volatile hydrocarbons and organic compounds are distilled therefrom. The volatile hydrocarbons are collected and the residue from the distillation is recovered.

14 Claims, No Drawings

METHOD OF PROCESSING ORGANIC WASTE INTO USEFUL PRODUCTS

BACKGROUND OF THE INVENTION

1. Field of the Invention

This invention relates to the processing of organic waste material and more particularly to the treating of organic waste material to form useful products.

2. Description of the Prior Art

It has been recognized that useful products may be made from garbage, sewage, sludge, wood, grain and the like. A typical process for treating waste is shown in U.S. Pat. No. 2,238,367 which converts municipal or industrial waste to liquid hydrocarbons, pitchy residue, ammonia, fuel gas and acetic acid and alcohols. Further, it has been recognized that the heating of garbage in retorts will produce an illuminating or heating gas as is disclosed in U.S. Pat. No. 548,342. This conversion of the organic waste material is a destructive distillation of the organic waste to produce lower molecular weight hydrocarbon fractions and gasses, oils and other volatilizable components.

The conversion of the waste material generally involves heating the material in the presence or absence of water to a temperature sufficient to break down the high molecular weight fractions to low molecular weight fractions and recovering these low molecular weight fractions which include greases, nitrogen compounds, hydrocarbons, oils, fats and the like. Many of these processes are taught by U.S. Pat. Nos. 1,777,449; 1,189,638; 1,122,474; 1,898,326; 2,205,699; 2,238,367; 3,362,887; 3,706,662; 3,714,038; 3,909,364; and 4,077,847.

In accordance with the present invention, a process for converting organic waste materials to usable organic products is provided which efficiently converts the organic waste to low molecular weight usable products in high yield and with minimal processing time.

BRIEF DESCRIPTION OF THE INVENTION

A method of treating organic waste involves slurrying the organic waste in water with a member selected from the group consisting of potassium carbonate, ammonium nitrate and ammonium nitrite. The slurry is heated at a temperature of 100° C. to 430° C. After heating, volatile hydrocarbons are distilled therefrom. The volatile hydrocarbons are collected and the residue from the distillation is recovered.

DETAILED DESCRIPTION OF THE INVENTION

The waste material useful in the practice of the invention includes garbage, grains, sewage waste, grass, sawdust, wood and other materials. The starting material can be substantially any discarded or spent product so long as it has a major amount of organic constituents. The potash (potassium carbonate), ammonium nitrate and ammonium nitrite may be used individually or in any combination so long as the weight ratio of the potassium carbonate, ammonium nitrate or ammonium nitrite is at a level of 50 to 300 parts by weight to 2400 parts by weight of organic waste material. The potassium carbonate, ammonium nitrate and ammonium nitrite provide for the efficient destruction of the high molecular weight material into smaller or lower molecular weight fractions.

The organic waste is slurried in water with the potassium carbonate, ammonium nitrate and/or ammonium nitrite. The slurry should be about 30 to 70 percent by weight organic waste material. The organic waste material is preferably pulverized or shredded prior to slurrying with water in order to get homogeneous mixing with the various slurry constituents. After a homogeneous slurry is prepared, it is charged to a suitable vessel and heated to 100° C. to 430° C., and more preferably 100° C. to 200° C., to break down the high molecular weight constituents. This heating process may be provided by high pressure steam at 400 to 800 psi or with harsh boiling of the slurry. Precooking temperature is dependent upon the condition of the organic waste used. For example, material which has been aged and partially decomposed due to biological degradation will require a lower cooking time and temperature, whereas material which has a large particle size or is composted will require a higher temperature and time.

After heating, the mixture is placed in a retort or other distillation apparatus and heated to a controlled point, i.e. up to about 200° C., and the hydrocarbons and other low molecular weight organic constituents are recovered through a standard distillation process. The products of the distillation may then be stored in appropriate receptacles.

The residue from the distillation can be refined through conventional techniques or additional ammonium nitrate, ammonium nitrite and/or potash may be added to the residue at a level of 25 to 150 parts by weight to 8,000 parts by weight of the residue.

Upon heating the residue with the ammonium nitrate, ammonium nitrite and/or potash therein, high molecular weight fractions present in the residue are broken down into lower molecular weight fractions and these lower molecular weight fractions may be distilled therefrom in the manner previously described. The residue from the second distillation may be processed and refined in accordance with known refining techniques available for high molecular weight petroleum-based products or the residue may be used as a pitch or asphalt-type material. Further, the residue may be added to an initial slurry of the organic waste material, water and potash, ammonium nitrate or ammonium nitrite.

Further, in accordance with the invention, the cooking temperature for the heating stage should be sufficiently high to provide boiling for about two hours and may be a precooking stage. Two hours is sufficient to break down the high molecular weight fractions into usable low molecular weight constituents.

In accordance with the invention, the products recovered include low molecular weight organic fractions useful for combustion in gasoline and diesel engines, organic nitrogen compounds, fertilizers, paraffins and greases, materials useful in the manufacture of paints, such as solvents, synthetic kerosene, synthetic gasoline, jet fuel, raw materials for synthetic rubber and the like. It is known that the products of processed organic waste can be used in much the same manner as the products of crude oil. Further, the complete pyrolysis of the residue yields carbon in the form of graphite, which can be used for electrodes.

The distilling step is done by known techniques and at known temperatures to recover the particular fractions desired.

The invention will be further illustrated by the following examples:

EXAMPLE 1

One thousand gallons of 30 percent solids water based sewage sludge is charged to a vessel capable of withstanding 1,500 psi equipped with a steam inlet and a steam outlet and a pressure relief valve. One hundred pounds of potash, 50 pounds of ammonium nitrate, and 50 pounds of ammonium nitrite are charged to the vessel and intimately mixed with the slurry. Steam is introduced into the vessel at a level of 400 to 800 psi and held in this range for two hours. This precooked mixture is then charged to a retort with a vapor recovery system and conventional apparatus used for the distillation of organic materials and hydrocarbons. The distillation is conducted in such a manner as to fractionate the low molecular weight organic constituents having a boiling point range equivalent to that of gasoline.

EXAMPLE 2

One thousand gallons of residue obtained according to the process of Example 1 are charged to a suitably sized vessel along with 50 pounds of potash, 25 pounds of ammonium nitrate and 25 pounds of ammonium nitrite and mixed until homogeneous. The vessel used is the same as the vessel used in Example 1 and the steam pressure and times are the same. This cooked residue is then charged to the distillation apparatus as described in Example 1 and the distillation is conducted accordingly. A high yield of low molecular weight hydrocarbon fractions and organic materials is recovered.

EXAMPLE 3

One thousand gallons of 30 percent solids water based farm manure, 100 pounds of potash, 50 pounds of ammonium nitrate, 50 pounds of ammonium nitrite and 150 pounds of finely shredded and pulverized garbage, 150 pounds of farm manure, and 100 gallons of ethyl alcohol are charged to the vessel described in Example 1. This mixture is processed in accordance with Example 1. The distillate recovered was used to power the internal combustion engine of a tractor and a saw mill. The saw mill was equipped with a four cylinder engine.

As can be seen from the foregoing examples, the present invention provides a method of processing organic waste materials which produces useful products. The addition of the ammonium nitrate, ammonium nitrite and/or potash effectively aids in the breaking down of the high molecular weight organic waste to low molecular weight usable products.

Although the invention has been described with reference to specific materials and processes, the invention is only to be limited insofar as is set forth in the accompanying claims.

I claim:
1. A method of treating organic waste comprising:
   A. slurrying the organic waste in water with a member selected from the group consisting of ammonium nitrate and ammonium nitrite;
   B. heating the slurry;
   C. distilling volatile hydrocarbons from the heated mixture;
   D. collecting the volatile hydrocarbons; and
   E. recovering the residue from the distillation.
2. The method of claim 1 wherein the ammonium nitrate or ammonium nitrite is present at a level of 50 to 300 parts by weight to 2400 parts by weight of organic waste material.
3. The residue recovered according to claim 2.
4. The method of claim 1 wherein the weight ratio of organic waste to water is 30 to 70 parts organic waste to 30 to 70 parts water.
5. The method of claim 1 wherein the precooking is done by heating with high pressure steam.
6. The method of claim 5 wherein said high pressure steam is between 400 to 800 psi.
7. The residue recovered according to claim 5.
8. The method of claim 1 including adding a member selected from the group consisting of ammonium nitrate, ammonium nitrite and potassium carbonate to said residue, heating the residue, and distilling volatile hydrocarbons therefrom.
9. The method of claim 8 wherein said ammonium nitrate, ammonium nitrite or potassium carbonate is present at a level of 25 to 150 parts by weight to 8000 parts by weight of the residue.
10. The method of claim 1 wherein said slurry is heated to a temperature of 100° C. to 430° C.
11. The method of claim 10 wherein said slurry is heated to a temperature of 100° C. to 200° C.
12. The method of claim 11 wherein said residue is refined.
13. The residue recovered according to claim 1.
14. The method of claim 1 including slurrying the organic waste with potassium carbonate.

* * * * *